(12) United States Patent
Dahan

(10) Patent No.: US 7,118,547 B2
(45) Date of Patent: Oct. 10, 2006

(54) GLAUCOMA DRAIN

(75) Inventor: Elie Dahan, Johannesburg (ZA)

(73) Assignee: Ioltechnologie-Production, Perigny (FR)

( * ) Notice: Subject to any disclaimer, the term of this patent is extended or adjusted under 35 U.S.C. 154(b) by 303 days.

(21) Appl. No.: 10/363,305

(22) PCT Filed: Aug. 31, 2001

(86) PCT No.: PCT/FR01/02714

§ 371 (c)(1),
(2), (4) Date: Oct. 28, 2003

(87) PCT Pub. No.: WO02/17832

PCT Pub. Date: Mar. 7, 2002

(65) Prior Publication Data

US 2004/0092856 A1    May 13, 2004

(30) Foreign Application Priority Data

Sep. 1, 2000    (FR)    ................... 00 11190

(51) Int. Cl.
*A61M 5/00*    (2006.01)
(52) U.S. Cl. .......................................... 604/8
(58) Field of Classification Search ............ 604/8–10, 604/264, 523, 284, 521, 294, 500, 540, 289, 604/265, 266; 606/107, 108, 1, 2, 4, 6; 623/4.1, 623/6.64, 11.11, 23.7–23.71, 902, 905, 907; 607/1–3, 88–89; 424/422–428, 477, DIG. 7
See application file for complete search history.

(56) References Cited

U.S. PATENT DOCUMENTS 4,037,604 A * 7/1977 Newkirk .................... 604/9
4,521,210 A    6/1985 Wong
4,787,885 A    11/1988 Binder
5,558,629 A * 9/1996 Baerveldt et al. .......... 604/8
5,601,094 A    2/1997 Reiss
5,626,558 A * 5/1997 Suson ......................... 604/8
5,882,327 A * 3/1999 Jacob ......................... 604/8
6,102,045 A * 8/2000 Nordquist et al. ......... 128/898
6,375,642 B1 * 4/2002 Grieshaber et al. ....... 604/294
6,783,544 B1 * 8/2004 Lynch et al. .............. 623/4.1

FOREIGN PATENT DOCUMENTS

| WO | 95/08310 | 3/1995 |
|---|---|---|
| WO | 95/35078 | 12/1995 |
| WO | WO 95/35078 | * 12/1995 |

\* cited by examiner

*Primary Examiner*—Patricia Bianco
(74) *Attorney, Agent, or Firm*—Young & Thompson

(57) ABSTRACT

A glaucoma drain for non-penetrating deep sclerotorny is made of non-resorbable and hydrophilic synthetic material. The drain is configured to be entirely covered by the scleral flap and totally inserted in the intrascleral space. It comprises a transverse bar (110) at one front end of the drain and a longitudinal body (120) extending longitudinally from said transverse bar. The transverse bar (110, 10) is configured to run along and cover the Schlemm's canal (CS) and the opposite ends are configured to penetrate beneath the deep sclera inside the Sclernm's canal. A hole (125) between the arms of the bar provides a target for possible YAG laser micro-punctures.

26 Claims, 2 Drawing Sheets

GLAUCOMA DRAIN

BACKGROUND OF THE INVENTION

1. Field of the Invention

The present invention relates to a glaucoma drain for facilitating the flow of aqueous humor through the trabeculo-descemetic membrane.

Glaucoma is a chronic, progressive and irreversible disease of having excessive intraocular pressure. When there is an obstacle to the evacuation of aqueous humor from the anterior chamber through a filter known as the trabeculum, the intraocular pressure increases and causes the progressive destruction of the nerve fibers. There are medical treatments whose efficacy proves to be insufficient in numerous cases in which solely surgery can enable the intraocular pressure to be reduced.

The purpose of surgical operation for the treatment of glaucoma is to create a mechanism for reducing the intraocular pressure. There are currently two main categories of drainage operation, penetrating and non-penetrating. The commonest surgery is penetrating surgery and is termed trabeculectomy. It consists in creating a fistula between the anterior chamber of the eye and a subconjunctival space. This operation requires, apart from opening the chamber, the formation of an aperture in the sclera using a scalpel, giving rise to complications which lead to a high number of failures.

2. Description of Related Art

The categories of non-penetrating surgical operations include viscanalostomy and deep sclerectomy, also termed ab externo trabeculectomy. Dr Robert Stegmman's viscanalostomy (J Cataract Refract Surg, vol. 25, 1999) comprises preparing a fornix based conjunctival flap and cutting a first parabolic flap of a third of the thickness of the sclera, and a second parabolic scleral flap of a depth of almost two thirds the thickness of the sclera which is later removed, de-roofing Schlemm's canal and injecting high viscosity non-crosslinked sodium hyaluronate into Schlemm's canal and subsequently under the outer flap after suturing. A scleral reservoir filled with sodium hyaluronate is thus formed under the outer flap. The physiological porosity of the juxtacanalicular trabecular meshwork and the descemetic membrane enable aqueous humor to be evacuated and the intraocular pressure to be reduced. However, the sodium hyaluronate is eliminated within five to six days and the reservoir rapidly fills up with fibrosis limiting the duration of effectiveness of the operation.

A development of this technique is presented in the PCT application WO 98/35640 which describes a pre-descemetic sclero-keratectomy implant of crosslinked hyaluronic acid having the form of a prism with a triangular base. This implant is supposed to occupy the surgically created space for a longer duration, but the volume of the implant reduces by half in four months and is totally resorbed subsequently.

According to another variant form of Dr Mermoud's deep sclerectomy, a glaucoma drain of cylindrical form is produced from lyophilized porcine collagen and is sutured in the deep scleral bed. The drain transports aqueous humor by capillarity. The superficial scleral flap does not close the posterior end of the cylindrical drain which is ill-adapted to the configuration of the scleral reservoir. The drain is resorbed in the month following the operation.

All these glaucoma implants and drains produced from crosslinked and non-crosslinked hyaluronic acid or from collagen are resorbable and thus do not constitute a truly long-lasting solution for draining aqueous humor from the anterior chamber so ensuring sustained reduction of the intraocular pressure. Moreover, these implants and drains of animal origin have a high manufacturing cost risk transmitting diseases, in particular viral diseases, and when they are of porcine origin or treated with porcine heparin, surgeons face refusal of patients on religious grounds.

The application WO 95/35078 describes a sclerectomy implant, with or without incision of the trabeculum, made from methylmethacrylate/vinylpyrrolidone copolymer with a high water content of the order of 40% It comprises an intra-scleral part adapted to be positioned against the trabeculum within an opening under the scleral flap and a sub-conjunctival part which emerges from the sclera and is lodged under the conjunctiva. The outer end of the implant pours aqueous humor under the conjunctiva and forms a bleb which is visible through the conjunctiva.

BRIEF SUMMARY OF THE INVENTION

The invention relates to a glaucoma drain which is able to ensure drainage for extended periods or even indefinitely and does not have the drawbacks of known glaucoma drains and other sclerectomy implants.

According to a first aspect of the invention, a glaucoma drain for deep non-penetrating sclerectomy is made from non-resorbable hydrophilic material and characterized in that it is configured to be entirely covered by a scleral flap and completely inserted inside the intrascleral space.

By virtue of the hydrophilic nature of the drain, it participates itself in the passage of aqueous humor from the trabeculo-descemetic membrane to the intrascleral space where it is taken up by venous circulation. Lodged entirely inside the intrascleral space, it does not promote the formation of blebs under the conjunctiva.

Preferably the non-resorbable hydrophilic material that is also non-pyrogenic, and, of course, biocompatible, is 38% polyhydroxyethyl methacrylate (38% PolyHEMA) or a hydrophilic acrylic. Apart from the fact that these materials are not resorbable, they do not cause fibrosis like other non-resorbable biocompatible materials, and notably silicone. Consequently, the drain makes it possible to maintain around itself a permanent intrascleral space under the scleral flap which is favorable to the flow of aqueous humor for an extended period. As the drainage site then has little fibrosis, it can be serviced, in particular to reestablish the flow of aqueous humor.

Preferably, the present glaucoma drain is of one piece and comprises a transverse bar and a body which extends longitudinally from the transverse bar.

According to a preferred embodiment, the drain is in the form of a T comprising the transverse bar arranged at the front end and the longitudinal body which extends rearwards from the center of the transverse bar.

According to another preferred feature, the transverse bar comprises on the posterior surface a pair of projections on each side of a median zone which form a channel.

For a deep non-penetrating sclerectomy, the transverse bar extends along and partially covers the trabeculo-descemetic membrane and the ends of the transverse bar pass under the intact sclera and inside Schlemm's canal. In this position, the front edge of the drain is close to, and in practice in contact with the trabeculo-descemetic membrane. The length of the body is such that its rear end does not extend beyond the intrascleral space.

According to a second embodiment, at least a front portion of the drain is convex, such that, when the arms of the transverse bar are in register with the trabeculo-descemetic membrane, the front convex edge tensions that membrane in order to stretch the mesh and to increase porosity, and thereby the flow from the anterior chamber to the intrascleral space.

Preferably, a hole is provided between the arms of the transverse bar and constitutes a target for aiming the micro-punctures in the trabeculo-descemetic membrane produced by YAG laser, when they prove necessary to improve the evacuation of aqueous humor to the intrascleral space.

The features and advantages of the invention will also emerge from the following description, made by way of example with reference to the accompanying drawings, in which:

DETAILED DESCRIPTION OF THE INVENTION

Figure 1:
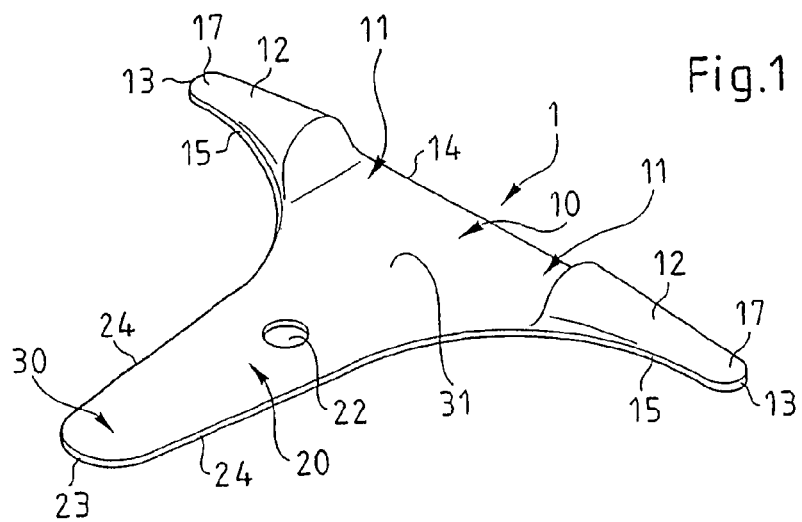
FIG. 1 is a perspective view of a glaucoma drain according to a first embodiment of the invention.
Figure 2:
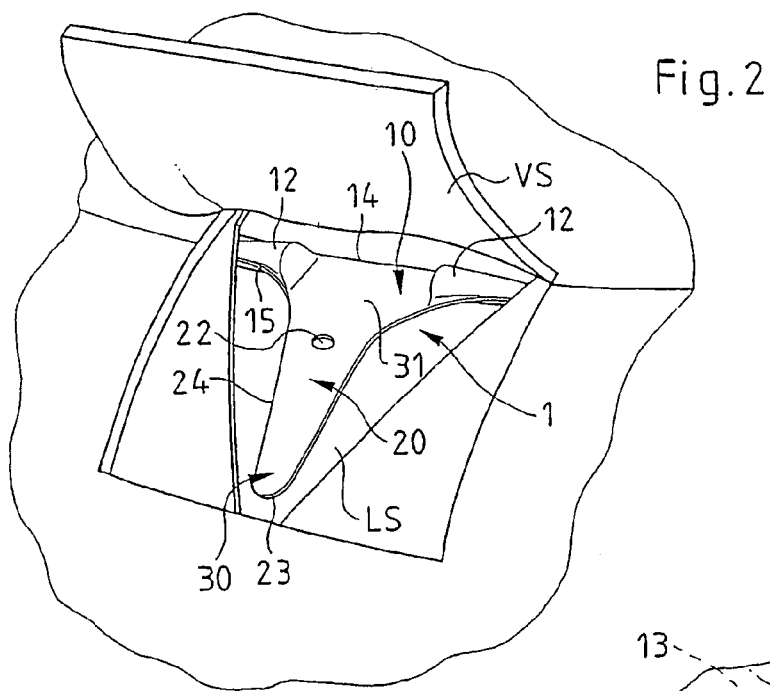
FIG. 2 is a view of the drain illustrated in FIG. 1 lodged in the intrascleral space implanted before closing the superficial scleral flap.
Figure 3:
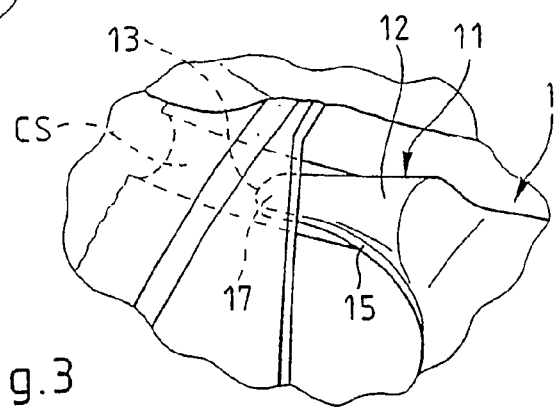
FIG. 3 is a detail view of FIG. 2.

The glaucoma drain 1, as illustrated in FIG. 1, is adapted to be implanted in the deep scleral bed (LS) in the course of a deep non-penetrating sclerectomy (see FIGS. 2 and 3).

According to the present invention, the glaucoma drain is produced from a biocompatible material that is non-resorbable, hydrophilic and non-pyrogenic. This hydrophilic material is permeable to the aqueous humor, such that aqueous humor can pass via the drain, in particular via its so-called front end, close to, and in practice in contact with the trabeculo-descemetic membrane to its so-called rear end, to be taken up by the circulatory system. The water content is preferably high. The 38% polyhydroxyethyl methacrylate (PolyHEMA) and the hydrophilic acrylic copolymer, such as that commercialized by the corporation Ioltech under the trade mark POLY-MEGMA™, are suitable.

Such an implant enables in situ drainage for an extended period of several years, or even indefinitely, without modification of the geometry of the drain since the material from which it is made is non-resorbable in the implantation environment. The hydrophilic material from which the drain is preferably made does not cause fibrosis and thus makes it possible to maintain around itself an intrascleral space which is favorable to the flow of aqueous humor. Similarly, as the site has little fibrosis, it can be serviced in case of need.

The drain 1 comprises a transverse bar 10 and a longitudinal body 20. The transverse bar 10 is situated at a so-called front end and comprises a pair of arms 11 extending in opposite directions. The longitudinal body 20 extends longitudinally towards the rear from the transverse bar. The general axis of the transverse bar 10 and that of the longitudinal body 20 are thus substantially perpendicular to each other. The longitudinal body preferably extends from the center of the latter and thus the drain 1 is generally T-shaped.

The outline of the drain is defined by the edges of the transverse bar 10 and of the longitudinal body 20 and comprises a front edge 14 of the transverse bar 10 extending between the rounded ends 13 of the bar which are continued by the lateral edges 15 of the other side of each of the arms and then by the lateral edges 24 of the longitudinal body 20 which terminate in a rounded end 23 at the rear end of the longitudinal body 20.

The anterior face, not illustrated, is substantially planar and thus without relief portions. The same applies to the posterior surface 30 of the longitudinal body 20 and of the median zone 31 of the transverse bar 10 between the arms 11.

According to a preferred embodiment, the posterior face of the arms 11 comprises a projection 12, of generally tapered form and preferably semi-frustoconical of which the apex is situated at the rounded end 13 of the respective arms.

The median zone 31 located between the projections 12 forms together with them a channel adapted to direct the flow on the posterior surface rearward along the longitudinal body 20.

An opening 22, preferably circular, is formed at mid-height of the body 20 and on the longitudinal thereof.

In practice, the width of the transverse bar 10 is slightly greater than that of the removed deep scleral flap, such that the end portions 17 of the arms 11 can be introduced under the intact sclera inside Schlemm's canal (CS), as illustrated in FIG. 2 and in detail in FIG. 3. The engagement by the end portions 17 of the respective arms ensures good positioning and orientation of the transverse bar 10 with respect to Schlemm's canal (CS) and the trabeculo-descemetic membrane. It is to be noted furthermore that the transverse bar 10 extends along and covers the trabeculo-descemetic membrane, the de-roofing of Schlemm's canal having been carried out beforehand, as positioned with respect to Schlemm's canal, and the front edge of the transverse bar is in contact throughout its length with the trabeculo-descemetic membrane (see FIG. 2).

Once the terminal portions 17 of the respective arms are in place, the body 20 may be sutured to the scleral bed (LS) by means of the opening 22. The superficial scleral flap (VS) may then be folded back and sutured followed by the conjunctival membrane.

The drain according to the invention ensures evacuation of aqueous humor into the intrascleral space formed under the scleral flap for an extended period by virtue of its both non-resorbable and hydrophilic nature. The drain makes it possible to maintain around itself a free permanent flow zone. Due to the high water content of the 38% polyHEMA or of the hydrophilic acrylic, aqueous humor may also pass via the drain to the circulatory system. The flow of aqueous humor is directed from the front end to the rear end and is favored by virtue of the channel defined between the projections on the posterior surface of the transverse bar. The configuration and the size of the drain enable implantation to be made entirely under the scleral flap and completely inside the intrascleral space.

If need be, the flow of aqueous humor may be increased by making micro-punctures by YAG laser in the region of the body of the drain 2 adjacent Schlemm's canal (CS). Moreover, the formation of a window in Schlemm's canal and the resulting positioning of the drain facilitate localization of the micro-punctures.

Nevertheless, according to an embodiment not illustrated, the projections may be eliminated such that the posterior face of the drain is substantially planar and thus without relief portions, like the anterior face. Similarly, although the T-shaped form, as illustrated, is preferred, other forms of the drain may be adopted. Whatever the case, the front edge must be positioned as illustrated in FIG. 2, that is to say close to and in practice in contact with the trabeculo-descemetic membrane.

In the hydrated state of the drain, the width of the transverse bar 10 between its opposite ends 13 is preferably 3 to 4 mm, or even greater, and more particularly approximately 4 mm. The height of the transverse bar defined between the front edge and the opposite lateral edge is of the order of 0.20 to 0.50 mm and preferably approximately 0.25 mm. The total height of the drain is preferably between 2.50 and 3.50 mm and in any case less than 4 mm, and the height of the body is approximately 2.75 mm.

The drain is preferably thin with a thickness of the order of 0.1 mm except for the thickness of the projection which is of the order of 0.30 mm. Thanks to that small thickness and the material it is made of, the drain may adapt itself to the curvature of the surface of the scleral bed. The thickness of the drain being of the order of that of the excised deep scleral bed, the drain may be entirely lodged inside the intra-scleral space after closing of the superficial scleral flap.

Figure 4:
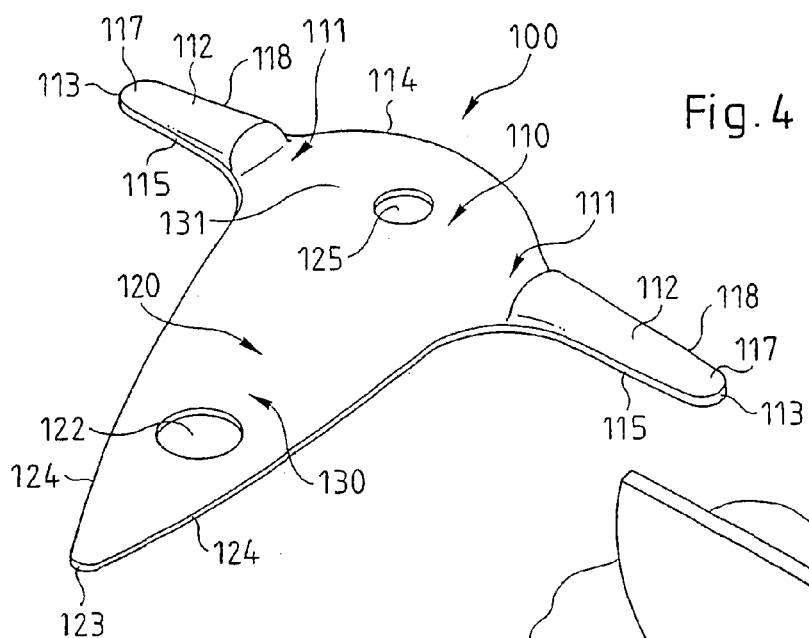
FIG. 4 is a perspective view of a glaucoma drain according to a second embodiment of the invention.
Figure 5:
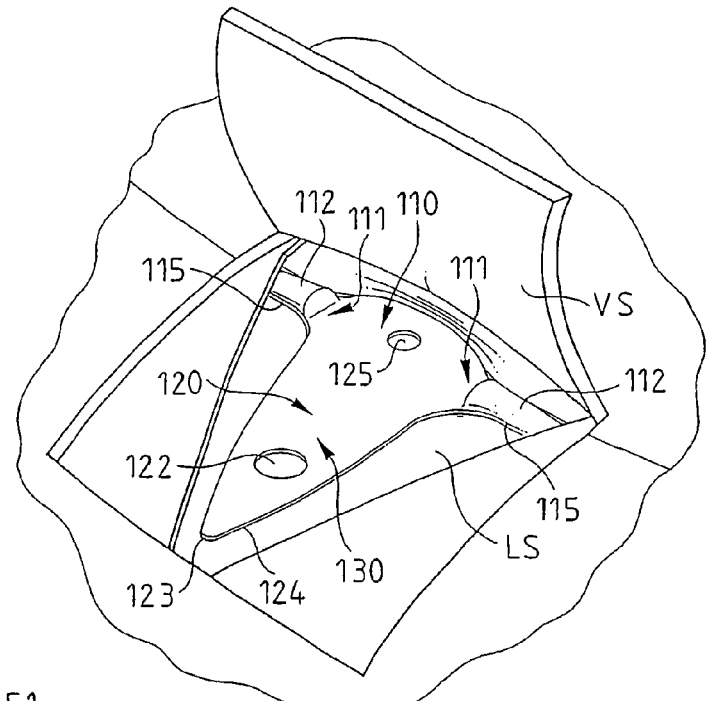
FIG. 5 is a view of the drain illustrated in FIG. 4 lodged in the intra-scleral space.

The glaucoma drain 100 according to a second embodiment, as illustrated in FIG. 4, is also adapted to be implanted in the deep scleral bed (LS) in the course of a deep non-penetrating sclerectomy (see FIG. 5).

The glaucoma drain 100 is also produced from the same biocompatible, non-resorbable, hydrophilic and non-pyrogenic material as that of the first embodiment and enables the same implantation to be carried out, with the same functions and advantages as those of the first embodiment.

The drain 100 comprises a transverse bar 110 and a longitudinal body 120. The transverse bar 110 is situated at a so-called front end and comprises a pair of arms 111 extending in opposite directions. The longitudinal body 120 extends longitudinally to a portion of the transverse bar. The general axis of the transverse bar 110 and that of the longitudinal body 120 are thus substantially perpendicular to each other. The longitudinal body preferably extends from the center of the latter and thus the drain 100 is generally T-shaped.

The outline of the drain is defined by edges of the transverse bar 100 and of the longitudinal body 120 and comprises a convex front edge 114 of the transverse bar 110 between the arms continued to the rounded ends 113 of the bar by straight lateral front edges 118 of the arms. The rounded ends 113 are continued by the lateral edges 115 parallel to the front lateral edges 118, on the other side of each of the arms and then by the lateral edges 124 of the longitudinal body 120 which terminate with a slightly rounded end at the rear end of the longitudinal body 123.

The anterior face, not illustrated, is substantially planar and thus without relief portions. The same applies to the posterior surface 130 of the longitudinal body 120 and of the median zone 131 of the transverse bar 110.

The posterior face of the drain comprises, on each side of the median zone 131, a projection 112, of generally tapered form and preferably semi-frustoconical of which the apex is situated at the rounded end 113 of the respective arms.

The median zone 131 located between the projections 112 forms together with them a channel adapted to direct the flow on the posterior surface between the projections 112 and along the longitudinal body 120.

An opening 122, preferably circular, is formed in the body 120 at approximately three-quarters of the distance between the center of the anterior edge and the posterior end of the body and on the longitudinal axis thereof.

In practice, the width of the transverse bar 110 is slightly wider than that of the removed deep scleral flap, such that the end portions 117 of the arms 111 can be introduced under the intact sclera inside Schlemm's canal (CS), as illustrated in FIG. 5. The engagement by the end portion 117 of the respective arms ensures good positioning and orientation of the transverse bar 110 with respect to Schlemm's canal (CS) and the trabeculo-descemetic membrane. The transverse bar 110 extends along and partially covers the trabeculo-descemetic membrane, the ablation of the roof of Schlemm's canal having been carried out beforehand As positioned with respect to Schlemm's canal, at least the convex front edge 114 of the transverse bar is in contact with the trabeculo-descemetic membrane (see FIG. 5) and the convex front edge 114 tensions it, such that its mesh, through stretching, increases the flow of aqueous humor through the trabeculo-descemetic membrane.

Once the terminal portions 117 of the respective arms are in place, the body 120 may be sutured to the scleral bed (LS) by means of the opening 122. The superficial scleral flap (VS) may then be folded back and sutured followed by the conjunctival membrane.

The drain according to this second embodiment ensures the evacuation of aqueous humor in the intrascleral space and improves its flow through the tensioned portion of the trabeculo-descemetic membrane.

In case of need, the flow of aqueous humor may be increased by making micro-punctures by YAG laser. For this purpose, a second hole 125 is provided between the arms 112 and substantially in alignment with them. This hole constitutes a reference point and a target through which the doctor can direct the YAG laser in order to localize the micro-punctures in the region of the trabeculo-descemetic membrane.

Preferably, the width of the transverse bar 110 between its opposite ends 113 is 3.5 to 4 mm, or even greater, and preferably approximately 4mm. The width of the median zone 113 between the inner ends of the projections 112 is greater in this embodiment and in practice is of the order of 1.7 mm. The height of the transverse bar defined between the parallel lateral edges 115, 118 is of the order of 0.20 to 0.30 mm and preferably approximately 0.25 mm. The total height of the drain is preferably between 3 and 3.75 mm and is preferably approximately 3.50 mm.

The drain is preferably thin with a thickness of the order of 0.15 mm except for the thickness of the projection which is of the order of 0.30 mm, and is sufficiently flexible to follow the curvature of the scleral bed (LS).

Figure 6:
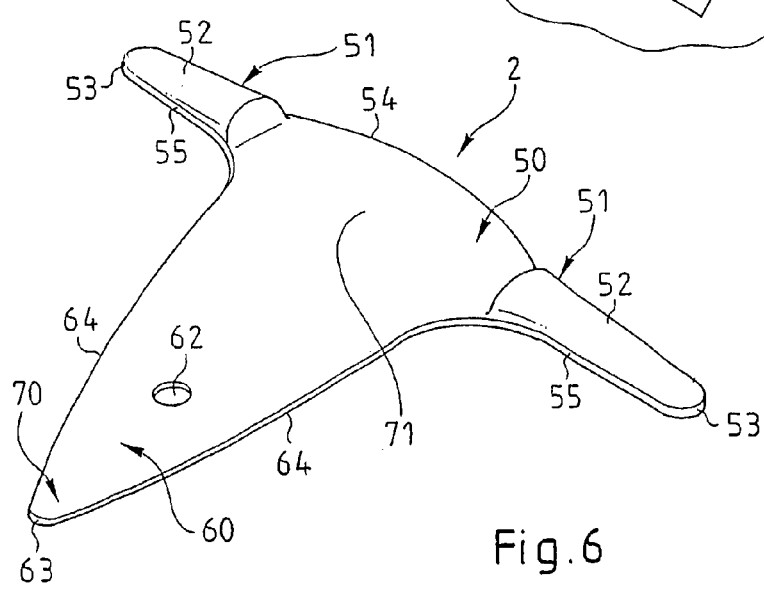
FIG. 6 is a perspective view of a glaucoma drain according to a third embodiment.

In a third embodiment illustrated in FIG. 6, the glaucoma drain 2 comprises a transverse bar 50 and a longitudinal body 60. The transverse bar 50 is situated at a so-called front end and comprises a pair of arms 51 extending in opposite directions. The longitudinal body 60 extends longitudinally to a portion of the transverse bar. The general axis of the transverse bar 50 and that of the longitudinal body 60 are thus substantially perpendicular to each other. The longitudinal body preferably extends from the center of the latter and thus the drain 2 is also generally T-shaped.

The outline of the drain is defined by the edges of the transverse bar 50 and of the longitudinal body 60 and comprises a front edge 54 comprising a central convex portion of the transverse bar 50 then continuing rectilinearly as far as the rounded ends 53 of the bar. The outline then follows the lateral edges 55 on the other side of each of the arms and then follows the lateral edges 64 of the longitudinal body 60 which converge towards a small rounded end 63 at the rear end of the longitudinal body 60.

According to a third embodiment, the drain comprises an anterior face, not illustrated in FIG. 6, which is substantially planar and thus without relief portions. The same applies to the posterior surface of the longitudinal body 60 and of the median zone 71 of the transverse bar 50.

According to a preferred embodiment, the posterior face 30 of the drain 2 comprises, on each side of the median zone 71, a projection 52, of generally semi-frustoconical form of which the apex is situated at the rounded end 53 of the respective arms.

The median zone 71 located between the projections 52 is thus in the same plane as the posterior surface 70 of the longitudinal body 60.

An opening 62, preferably circular, is formed at approximately two-thirds of the distance between the edge 52 and the rounded end 63 and is located on the longitudinal axis of the body.

Similarly, due to the high water content of the 38% polyHEMA or of the hydrophilic acrylic, the aqueous humor may also pass via the drain itself to the uveoscleral circulatory system. Finally, as in the first two embodiments, by virtue of the fact that the drain is non-resorbable and hydrophilic, a permanent space is produced around the body of the drain, despite the inevitable scarring between the scleral bed and the superficial scleral flap.

In the hydrated state, the width of the transverse bar 50 between its opposite ends 53 is preferably 3.5 to 4.5 mm and more particularly of the order of 3.5 mm. The length of each of the arms of the transverse bar is of the order of 1 mm. The height of the transverse bar defined between the opposite edges is of the order of 0.2 to 0.4 mm and preferably approximately 0.25 mm. Similarly, the total height of the drain is preferably between 3 and 4 mm, and more particularly 3.5 mm. The width of the drain adjacent the slit made in Schlemm's canal is preferably between 1.3 and 1.8 mm and more particularly of the order of 1.5 mm, that is to say of the order of 0.1 mm less than the width of the slit.

The thickness of the drain is of the order of 0.1 mm except at the projections where it is of the order of 0.30 mm.

The glaucoma drain of this third embodiment may thus be implanted in the same manner as in accordance with the first embodiment.

Whatever the form of the glaucoma drain produced for example from 38% polyHEMA or from hydrophilic acrylic, it may be manufactured according to usual processes in the field of intraocular implants. Preferably, the drain is lathe cut.

Once produced and sterilized, the drain is packaged in a pouch or vial containing an isotonic solution such as 0.9% NaCl. The drain may be mounted into a support (not shown) so that it can be manipulated more easily.

Naturally, the present invention is not limited to the form of the embodiment described and represented, but covers any variant forms. Although the T-shaped form of each of the illustrated embodiments is preferred for the two applications described, other configurations may be adopted. Similarly, other non-resorbable and hydrophilic materials may be used to produce flexible intraocular implants.

The invention claimed is:

1. A glaucoma drain for deep non-penetrating sclerectomy, the glaucoma drain being made of hydrophilic non-resorbable synthetic material and being configured to be covered by the scleral flap and to be inserted inside an intrascieral space, the glaucoma drain comprising a transverse bar at a front end thereof and a longitudinal body extending longitudinally from said transverse bar, opposite ends of said transverse bar being configured to penetrate inside Schlemm's canal.

2. A glaucoma drain according to claim 1, wherein the glaucoma drain is generally T-shaped.

3. A glaucoma drain according to claim 2, wherein the transverse bar is configured to extend along and cover Schlemm's canal.

4. A glaucoma drain according to claim 2, wherein the drain is made of 38% polyHEMA or hydrophilic acrylic.

5. A glaucoma drain according to claim 2, wherein the transverse bar comprises at least one projection on a posterior face of the drain.

6. A glaucoma drain according to claim 1, wherein the transverse bar comprises at least one projection on a posterior face of the drain.

7. A glaucoma drain according to claim 6, wherein a pair of projections is disposed on respective arms defined by the transverse bar and form a channel therebetween.

8. A glaucoma drain according to claim 7, wherein the section of each of the projections tapers towards an apex situated near respective terminal portions of the transverse bar.

9. A glaucoma drain according to claim 7, wherein a hole is defined between arms of the bar and defines a target for locating laser micropunctures.

10. A glaucoma drain according to claim 1, wherein the drain is made of 38% polyHEMA or hydrophilic acrylic.

11. A glaucoma drain according to claim 1, the longitudinal body tapers from the transverse bar towards its free end.

12. A glaucoma drain according to claim 1, wherein the width of the transverse bar is between approximately 3 and 4 mm.

13. A glaucoma drain according to claim 1, wherein the drain comprises an opening for suturing the drain to a deep scleral flap.

14. A glaucoma drain according to claim 1, wherein the total length of the drain is between approximately 2.5 and 3.50 mm.

15. A glaucoma drain according to claim 1, wherein a front edge of the glaucoma drain is substantially straight and is configured to be in contact with the trabeculo-descemetic membrane.

16. A glaucoma drain according to claim 1, wherein a front edge of the glaucoma drain has a convex portion.

17. A glaucoma drain according to claim 1, wherein the drain is made of 38% polyHEMA or hydrophilic acrylic.

18. A glaucoma drain for deep non-penetrating sclerectomy, the glaucoma drain being made of hydrophilic non-resorbable synthetic material and being configured to be covered by the scleral flap and to be inserted inside an intrascleral space, the glaucoma drain comprising a transverse bar at a front end thereof and a longitudinal body extending longitudinally from said transverse bar, a front edge of the transverse bar projects anteriorly in order to tension the trabeculo-descemetic membrane.

19. A glaucoma drain according to claim 18, wherein the projecting front edge is convex and extends between front edges of the lateral arms.

20. A method for reducing intraocular pressure in the anterior chamber of the eye comprising the steps of: providing a hydrophilic, non-resorbable glaucoma drain having a longitudinal body and a transverse bar at a front end of the longitudinal body, performing a deep non penetrating sclerectomy, thereby forming a scleral flap and an interscleral space, introducing the drain into the intrascleral space and introducing opposite ends of the transverse bar inside Schlemm's canal and closing the scleral flap.

21. A method according to claim 20, wherein the space defined around the drain defines a substantially permanent flow path for aqueous humor.

22. A method according to claim 20, wherein the ends of the transverse bar are inserted under the deep sclera inside Schlemm's canal after Schlemm's canal is de-roofed.

23. A method according to claim 20, wherein the front edge of the drain is brought into contact with the trabeculo-descemetic membrane.

24. A method according to claim 20, wherein the front edge of the drain has a forward bulge for tensioning the trabeculo-descemetic membrane to increase the flow of aqueous humor through the trabeculo-descemetic membrane.

25. A method according to claim 20, further comprising directing a YAG laser in the region of the drain and adjacent Schlemm's canal to provide micro-punctures for enhancing flow of aqueous humor from the anterior chamber.

26. A method according to claim 20, wherein the drain has a hole between arms of the transverse bar defining a target for aiming the YAG laser to localize the micro punctures in the region of the trabeculo-descemetic membrane.

* * * * *